(12) United States Patent
Gugler et al.

(10) Patent No.: US 9,198,761 B2
(45) Date of Patent: Dec. 1, 2015

(54) JOINT SOCKET IMPLANT

(75) Inventors: Christian Gugler, Frauenfeld (CH);
Martin Schmidt, Wängi (CH); Andreas Meyenhofer, Schlattingen (CH)

(73) Assignee: Jossi Holding AG, Islikon (CH)

( * ) Notice: Subject to any disclaimer, the term of this patent is extended or adjusted under 35 U.S.C. 154(b) by 11 days.

(21) Appl. No.: 14/006,269

(22) PCT Filed: Mar. 21, 2012

(86) PCT No.: PCT/EP2012/054991
§ 371 (c)(1),
(2), (4) Date: Sep. 19, 2013

(87) PCT Pub. No.: WO2012/126944
PCT Pub. Date: Sep. 27, 2012

(65) Prior Publication Data
US 2014/0012391 A1    Jan. 9, 2014

(30) Foreign Application Priority Data

Mar. 21, 2011   (EP) .................................. 11159050

(51) Int. Cl.
*A61F 2/32* (2006.01)
*A61F 2/34* (2006.01)
*A61F 2/30* (2006.01)

(52) U.S. Cl.
CPC ............... *A61F 2/34* (2013.01); *A61F 2/30771* (2013.01); *A61F 2002/3083* (2013.01);
(Continued)

(58) Field of Classification Search
CPC ................ A61F 2/30771; A61F 2002/30322; A61F 2002/3083; A61F 2002/30904; A61F 2002/30421; A61F 2002/3472; A61F 2002/3012; A61F 2002/30289; A61F 2002/30291; A61F 2002/30293; A61F 2002/30859; A61F 2002/30961; A61F 2002/30874; A61F 2/34; A61F 2002/20
USPC ............................................ 623/22.21, 22.31
See application file for complete search history.

(56) References Cited

U.S. PATENT DOCUMENTS 4,662,891 A * 5/1987 Noiles ......................... 623/22.31
4,834,759 A * 5/1989 Spotorno et al. ............. 623/22.3

(Continued)

FOREIGN PATENT DOCUMENTS

DE         2259313        6/1973
DE         3535959        4/1987

(Continued)

*Primary Examiner* — Alvin Stewart
(74) *Attorney, Agent, or Firm* — Davis & Bujold, P.L.L.C.; Michael J. Bujold (57) ABSTRACT

The invention relates to a ball-and-socket implant (I), in particular an acetabular implant, preferably in the shape of a spherical cup shell, said implant having at least one region with a surface structure (2, 7). The at least one region extends between the equator and the pole of the spherical cup shell. The surface structure comprises a plurality of structural elements (6), each of which is formed by a plurality of intersecting ridges (3, 8) with opposite inclinations. The number of structural elements (6) on the equator (5) or on a circle of latitude near the equator is the same as on a circle of latitude near the pole. The ridges (3, 8) have a curvature such that the inclination of the ridges with respect to the circles of latitude, and thus an angle between a tangent of the ridge curvature and a circle of latitude, continuously increases from the equator (5) to the pole (4).

18 Claims, 10 Drawing Sheets

(52) U.S. Cl.
CPC .............. *A61F 2002/30322* (2013.01); *A61F 2002/30825* (2013.01); *A61F 2002/30843* (2013.01); *A61F 2002/30904* (2013.01)

(56) References Cited

U.S. PATENT DOCUMENTS

| | | | | |
|---|---|---|---|---|
| 4,865,603 | A * | 9/1989 | Noiles | 623/23.5 |
| 4,892,549 | A * | 1/1990 | Figgie et al. | 623/22.23 |
| 5,147,407 | A * | 9/1992 | Tager | 623/22.27 |
| 5,310,408 | A * | 5/1994 | Schryver et al. | 623/22.37 |
| 5,358,532 | A * | 10/1994 | Evans et al. | 623/22.23 |
| 5,571,201 | A * | 11/1996 | Averill et al. | 623/22.22 |
| 5,755,799 | A * | 5/1998 | Oehy et al. | 623/18.11 |
| 6,146,425 | A * | 11/2000 | Hoermansdoerfer | 623/22.31 |
| 6,221,076 | B1 * | 4/2001 | Albrektsson et al. | 606/80 |
| 6,224,633 | B1 * | 5/2001 | Kalberer et al. | 623/22.24 |
| 6,231,612 | B1 * | 5/2001 | Balay et al. | 623/22.31 |
| 6,827,740 | B1 * | 12/2004 | Michelson | 623/17.11 |
| 6,988,015 | B1 * | 1/2006 | Schopf et al. | 700/98 |
| 7,513,913 | B2 * | 4/2009 | Hoermansdoerfer | 623/22.31 |
| 8,070,823 | B2 * | 12/2011 | Kellar et al. | 623/23.4 |
| 8,206,454 | B2 * | 6/2012 | Hormansdorfer | 623/22.31 |
| 8,894,717 | B2 * | 11/2014 | Birkbeck et al. | 623/22.21 |
| 9,005,307 | B2 * | 4/2015 | Kellar et al. | 623/23.4 |
| 2006/0178750 | A1 * | 8/2006 | Chieng | 623/22.27 |
| 2007/0162146 | A1 * | 7/2007 | Balay et al. | 623/22.21 |
| 2008/0228282 | A1 * | 9/2008 | Brodowski | 623/22.11 |
| 2009/0192609 | A1 * | 7/2009 | Klabunde et al. | 623/16.11 |
| 2010/0280517 | A1 * | 11/2010 | Cawthan et al. | 606/81 |
| 2011/0264231 | A1 * | 10/2011 | Theillez et al. | 623/22.32 |
| 2012/0095569 | A1 * | 4/2012 | Kellar et al. | 623/23.43 |

FOREIGN PATENT DOCUMENTS

| | | |
|---|---|---|
| DE | 10106863 | 9/2002 |
| EP | 0839016 | 5/1998 |
| EP | 2338443 | 6/2011 |
| GB | 2268408 | 1/1994 |
| WO | 97/39702 | 10/1997 |

* cited by examiner

JOINT SOCKET IMPLANT

The present invention relates to a joint socket implant as per the preamble of claim 1.

A multiplicity of surface structures are known for the improved anchoring of implants, in particular endoprostheses in bones. These range from roughened-up surfaces to equipping the surface with complex structure elements.

It is advantageous, particularly in the field of hip-joint prostheses, if the implant parts, in particular the joint socket applied to the hip bone, can be anchored in the bone such that they cannot be ripped out or rotated. While one group of joint sockets is anchored by screws, a second group is attached by means of bone cement or by hammering.

In order to improve the ripping-out property and the fixing against rotation of a joint socket attached by means of bone cement or by hammering, the surface of such sockets is usually provided with structure elements. Forces occurring in the process are distributed uniformly by these structure elements, which thereby prevent a rotation or even the ripping out of the joint socket. In the case of hammering, the structure elements ensure good growing into the bone.

A person skilled in the art is aware of a multiplicity of different surface structures. Here, the surface structures are usually worked into the surface of the implants by cutting methods.

By way of example, EP 0 839 016 discloses a hip-joint socket with a surface structure with rhomboid elevations. The elevations are delimited by intersecting, helical threads with opposing pitches. Here, the depth of the threads reduces from the equator to the pole.

DE 101 06 863 describes an implantable hip socket which has a structure in the form of pyramid tips on the surface. The pyramid tips are produced by working in right-handed thread profiles and left-handed thread profiles by cutting. The profile height of these thread profiles reduces from the entry plane of the socket toward the pole region thereof.

As a result of combining thread and spherical cap, the number of elevations reduces markedly toward the pole, reducing the anchoring of the joint socket in the bone. Furthermore, the anchoring in the bone is additionally weakened by the reducing depth of the threads.

An object of the present invention is to develop a surface structure for joint socket implants, which overcomes the disadvantages of the known and which, in particular, enables good anchoring of the joint socket in the bone and is simple to produce. This object is achieved by a joint socket implant in accordance with claim 1.

The joint socket implant according to the invention preferably has a shape of a spherical cap shell and has at least one region with a surface structure. The at least one region extends between the equator and the pole of the spherical cap shell. The surface structure comprises a multiplicity of structure elements, which are each formed by a multiplicity of intersecting grooves with opposite pitches. The number of structure elements on the equator or a circle of latitude close to the equator is the same in this case as on a circle of latitude close to the pole. The grooves have such curvature that the pitch of the grooves in relation to the circles of latitude, and hence an angle between a tangent of the groove curvature and a circle of latitude, increases continuously from the equator to the pole.

In particular, this means that the grooves have such a profile that the pitch of the grooves in relation to the circles of latitude, and hence an angle between a tangent of the groove profile and a circle of latitude, increases continuously from the equator to the pole. It is understood that the angle between the tangent of the groove profile and a circle of latitude in this case need not necessarily increase constantly from the equator to the pole.

Here curvature denotes a profile of the directional changes when traversing the curve. The present curvature as per the claim 1s in this case understood to be that additional portion of curvature which goes beyond curvature prescribed by the curved surface on which the grooves are formed. The profile of the grooves of the joint socket implant according to the invention should be distinguished from sphere loxodromes, which always intersect the circles of latitude at the same angle, i.e. have a constant pitch (but nevertheless have predetermined spatial curvature due to the curved surface).

The joint socket implant according to the invention is preferably a hip-joint socket implant. The joint socket implant preferably substantially has the form of a spherical cap shell, particularly preferably the form of a hemispherical shell. It is understood that the spherical cap shell can have deviations from a pure spherical shape. In particular, the cap can have e.g. a depression or bore in the pole region for manipulation purposes. The cap can likewise be flattened in the pole region in order to promote desired clamping of the shell significantly in the equatorial region during the implantation.

The spherical cap shell has an outer convex surface which rests on the bone when the joint socket is inserted into the bone. Furthermore, the spherical cap shell has an inner, concave or approximately concave surface, into which a bearing shell can be inserted. The joint socket implant has a wall between these two surfaces, the thickness of which wall is preferably the same everywhere, i.e. the radii of the outer and the inner surface have the same center point and are both substantially constant. Alternatively, the thickness of the wall can also change; for example, the inner surface can consist of several faces which are at a specific angle to one another or the outer surface can have a flattening in the pole region.

The size of the spherical cap shell can vary depending on the patient for whom the joint socket implant is provided or on the application location, for example in the hip or shoulder joint.

Furthermore, the joint socket implant has at least one region with a surface structure. This region is situated between the equator and the pole and preferably extends over the whole circumference of the joint socket implant. Depending on the embodiment, the region has different extents between equator and pole of the joint socket implant. This region extends particularly preferably over at least half of the surface from the equator in the direction of the pole.

Within the meaning of the application, the "equator" is understood to be the opening of the spherical cap shell, while the position which corresponds to the apex of the spherical cap shell is referred to as "pole".

Within the meaning of the present application, a "region close to the equator" is situated closer to the equator than to the pole, while a "region close to the pole" is situated closer to the pole than to the equator of the joint socket implant.

The surface structure comprises a multiplicity of structure elements. The structure elements are formed by intersecting grooves. The grooves have preferably been produced in the surface by a cutting method, such as e.g. milling or impact cutting.

The grooves preferably have opposite pitches, i.e. point in opposite circumferential directions in respect of a pole axis of the spherical cap shell. In other words, in relation to the equator, individual grooves extend to the left while others extend to the right. Each structure element is delimited by two neighboring grooves extending to the left and two neighboring grooves extending to the right, which grooves intersect.

Each structure element therefore has a substantially rhomboid area or outline if the curvature of the boundaries due to the groove curvature, which is negligible in relation to the size of the structure elements, is ignored.

The grooves are preferably configured in such a way that the number of structure elements on the equator or a circle of latitude close to the equator is the same as on a circle of latitude close to the pole. Within a region with surface structure, the number of structure elements on any circle of latitude of the joint socket implant is therefore the same.

The grooves with the same pitch direction, i.e. with the same circumferential direction, preferably all have the same curvature or the same curved profile. It is understood that, depending on requirements, the grooves with different circumferential directions, i.e. with opposite pitch directions, can advantageously also have a different curvature or a different profile. By way of example, at a specific circle of latitude, the grooves with the same pitch direction can have a pitch which differs (also in terms of magnitude) from a pitch of the grooves with opposite pitch directions.

So that the number of structure elements on the equator or a circle of latitude close to the equator is the same as on a circle of latitude close to the pole, the pitch of the grooves in relation to the circles of latitude, and hence the angle between a tangent of the groove curvature or of the groove profile and a circle of latitude, increases continuously, but not necessarily constantly, from the equator to the pole.

At the same time, the radius of curvature preferably decreases continuously from the equator to the pole, i.e. the curvature of the groove increases continuously to the pole. The pitch profile can be selected in such a way that the distance between two grooves with the same pitch direction remains constant from the equator in the direction of the pole.

The outline of the structure elements changes from the pole toward the equator. As a result of the pitch of the grooves which increases toward the pole, the structure elements which lie on the same meridian have an extent parallel to the circles of latitude which constantly increases from the pole in the direction of the equator. By contrast, an extent in the direction perpendicular to the circles of latitude reduces.

The pitch profile of the grooves can be selected in such a way that an area content of the surface area of the structure elements is similar as possible or approximately equal close to the equator and the pole so that, overall, this results in an optically largely homogeneous surface structure.

Since the joint socket is inserted into the bone in a direction at right angles to the circles of latitude, this is advantageous in that each structure element must cut a little deeper into the bone in the direction parallel to the circles of latitude, which increases the anchoring of the joint socket implant in the bone.

Two neighboring grooves with the same pitch direction or circumferential direction preferably have a largely constant distance from one another over their whole length. This can be achieved by a suitable selection of the pitch profile of the grooves as a function of the distance of the respective circle of latitude from the equator. Neighboring grooves with the same pitch direction preferably have the same distance in a pairwise fashion, that is to say any neighboring pair.

It is understood that, as a result of the constant distance, the grooves cannot extend all the way to the pole but only to a circle of latitude closest to the pole, namely to where the pitch angle between grooves and circle of latitude reaches 90°. The closest possible circle of latitude to the pole is in this case determined on the basis of a number of factors such as e.g. the spacing of the grooves, the number of the grooves, the width of the grooves, etc.

The grooves from the region close to the equator to the region close to the pole preferably have a constant depth in the at least one region. As a result, the structure elements also have a constant height. As a result, the anchoring is of the same quality over the whole surface of the joint socket implant. Moreover, such a configuration enables equally good stability of the joint socket implant in the bone along the pole axis and also against rotation or tilt.

The angle between a tangent of the groove curvature or the groove profile of each groove and a specific circle of latitude preferably has the same magnitude. This results in a particularly regular configuration of the structure elements and hence also of the surface structure, which enables a particularly regular anchoring of the joint socket implant, for example by growing into the bone or by anchoring in the bone cement.

The structure elements are advantageously configured by neighboring grooves with different flank shapes, groove depths, groove widths, groove spacing and the groove number.

The structure elements particularly preferably have the shape of a pyramid or a pyramid frustum. The shape of the structure elements is predetermined by the profile of the grooves, and so the shape of the structure elements can be modified by a suitable choice of the groove profile. In particular, a flank shape of the structure elements can be prescribed by the profile of the grooves. Alternatively, the structure elements have any polyhedral or else rounded shape. After producing the structure elements by the grooves, these can also be post-processed, e.g. by milling or by reshaping methods.

In the meridian cross section, the structure elements are preferably inclined in the direction of the equator. That is to say that at least that side of the structure element which points in the direction of the equator has a steeper pitch or is even overhanging. The saw tooth-like cross section of the structure elements along a meridian achieved thereby additionally increases the force required to rip out the joint socket implant.

The joint socket implant preferably has at least a second region with a surface structure. The surface structures preferably comprise a multiplicity of structure elements in all regions, which structure elements are formed in each case by a plurality of intersecting grooves with opposite pitches, largely analogously to the first region. The surface structures of the regions in this case preferably have different configurations (e.g. depth of the grooves, number of the grooves, extent of the grooves, profile of the grooves, spacing of the grooves, etc.). The two regions with surface structures advantageously have a different number of structure elements and/or grooves and/or the structure elements differ in terms of their configuration (e.g. flank shape or depth of the grooves). Furthermore, the joint socket implant can preferably also have more than two regions with different surface structures, such as e.g. three, four, five or more regions. The regions can all have different extents between equator and pole of the joint socket implant or else all have the same extent. As a result, the joint socket implant can be equipped with regions which have anchoring properties that are adapted to specific bone regions.

The joint socket implant according to the invention particularly preferably comprises the first region with a first surface structure with structure elements with surface structures inclined in the direction of the equator in the meridian cross section in a region close to the equator and the second region with a second surface structure with structure elements in the form of pyramids in a region close to the pole.

Such a configuration of the joint socket implant is advantageous in that the region close to the equator additionally increases the force required to rip out the inserted joint socket implant as a result of the saw tooth-shaped structure elements, while the pyramidal structure elements in the region close to the pole secure the joint socket implant in an optimum fashion against twisting and/or tilting and ensure optimal growing into the bone in this region as well.

In a region of the surface structure close to the equator, the grooves preferably form an angle of less than 90° with a circle of latitude. This angle preferably lies in a region from 10° to 60°, particularly preferably in a region from 15° to 50°. This angle increases continuously toward the pole due to the curvature of the grooves, i.e. due to the pitch profile.

The at least one region with a surface structure on the equator or on the circle of latitude close to the equator and on the circle of latitude close to the pole, respectively, preferably has 10 to 100 structure elements.

The structure elements preferably have outlines with side lengths of approximately 0.2-5 mm.

The structure elements particularly preferably have an outline which is approximately rhomboid. In contrast to a rhombus, the side edges, i.e. the grooves delimiting the area, are not straight but have a curve. However, for simplifications purposes, it is possible to assume a rhombus shape as an approximation. As a result of the curvature, or the profile of the grooves, the length of the diagonals of the areas of the structure elements parallel to the meridians increases from the equator in the direction of the pole, while the diagonals parallel to the circles of latitude reduce. That is to say, a structure element has a different outline, depending on the vicinity to the equator or the pole.

The structure elements which are closer to the pole have an outline which, in the direction of the meridians, is longer than in the direction of the circles of latitude. The shape of the areas, i.e. the outline, in this case simplifies the insertion of the joint socket implant since the structure elements can cut into the bone more easily.

The different geometries of the outlines of the structure elements are moreover advantageous in that those structure elements which have a larger extent in the direction of the meridians secure the joint socket implant well against rotating and tilting while those structure elements which have a greater extent in the direction of the circles of latitude secure the joint socket implant better against being ripped out.

The grooves preferably have a symmetric or an asymmetric cross section. As a result, it is additionally possible to modify the shape of the structure elements, in particular the shape of the flanks.

Further aspects and details of the invention emerge from the following description of examples and figures. In detail.

Figure 1:
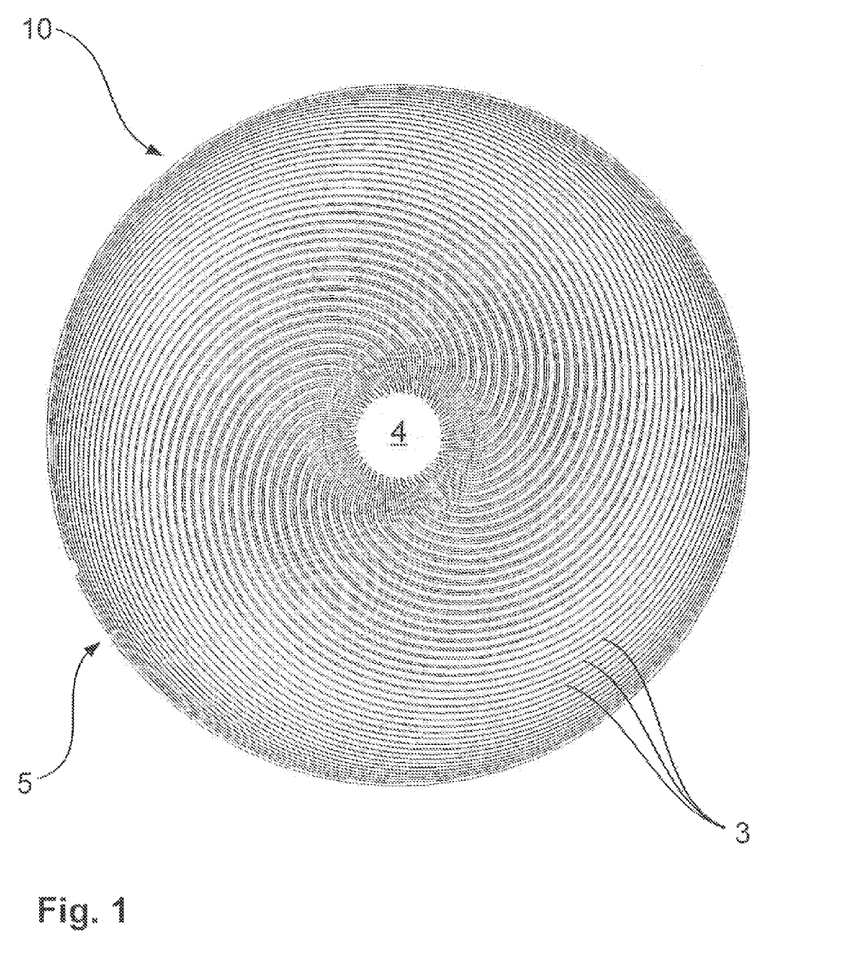
FIG. 1 shows a plan view of an intermediate product during the production of a joint socket implant with grooves.
Figure 2:
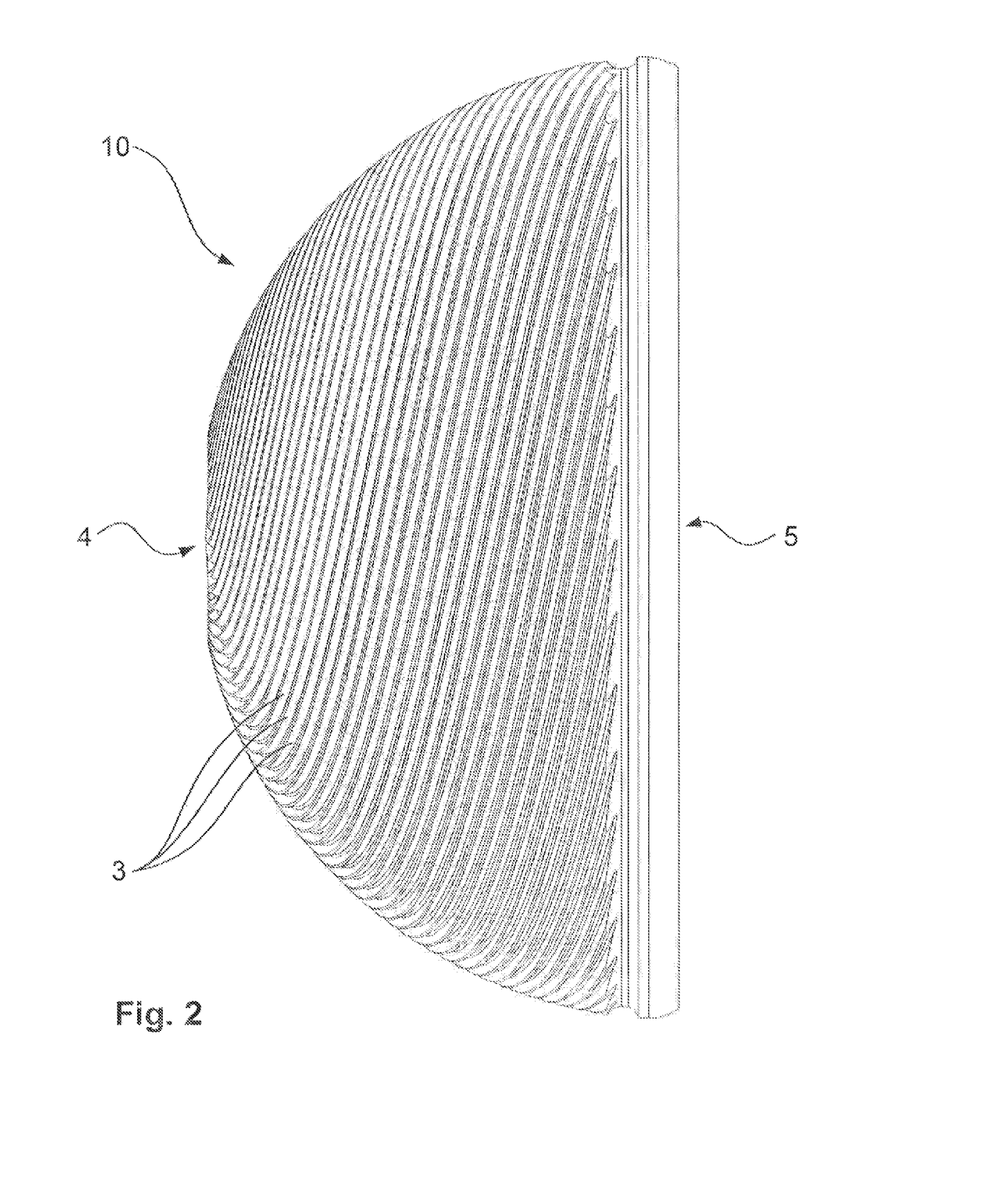
FIG. 2 shows a side view of the intermediate product from FIG. 1.

FIG. 1 shows a plan view of an intermediate product 10 during the production of a joint socket implant 1, which only has grooves 3 directed to the left, i.e. with a left-hand circumferential direction. FIG. 2 shows a side view of the same intermediate product 10. The intermediate product 10 is in the form of a spherical cap shell and has a pole 4 and an equator 5. In this exemplary embodiment, the spherical cap shell corresponds to a hemispherical shell. The intermediate product 10 is the result of a first processing step in the production of a joint socket implant according to the invention, during which all grooves 3 are initially only introduced in one pitch direction.

Figure 3:
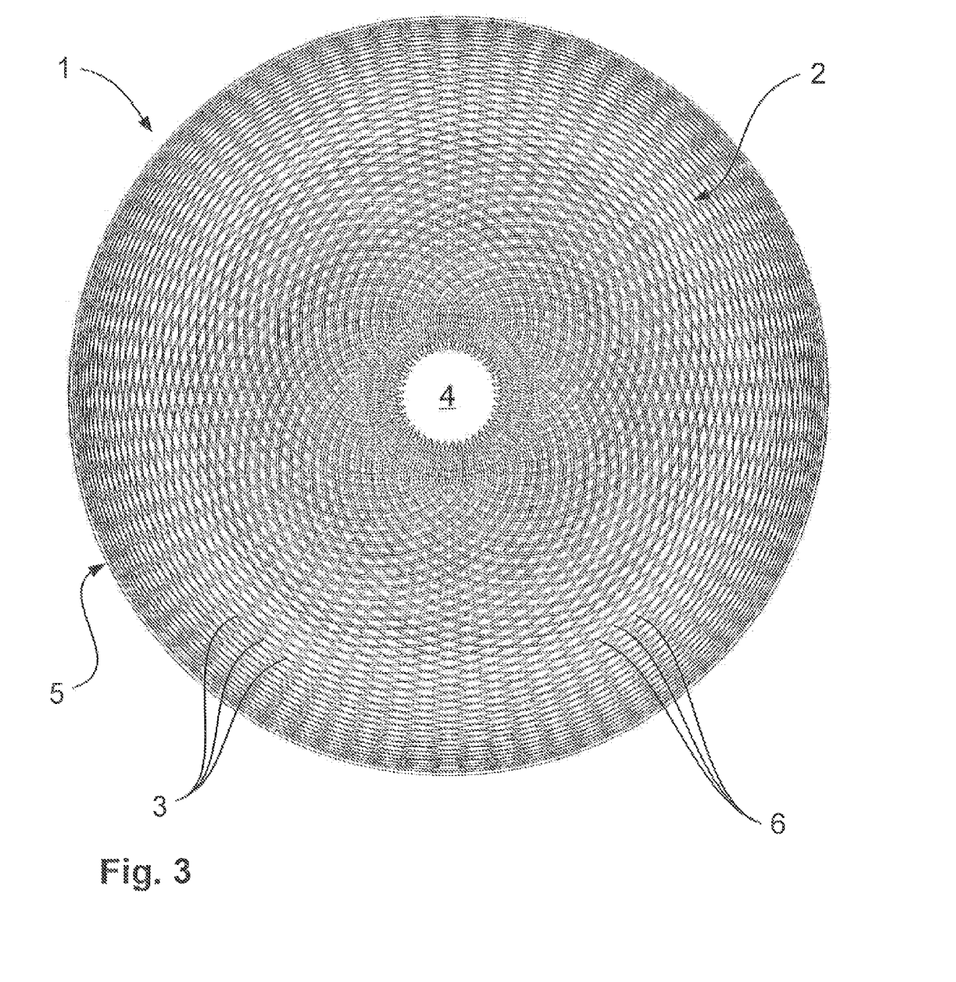
FIG. 3 shows a plan view of a joint socket implant according to the invention, with a region with a surface structure.
Figure 4:
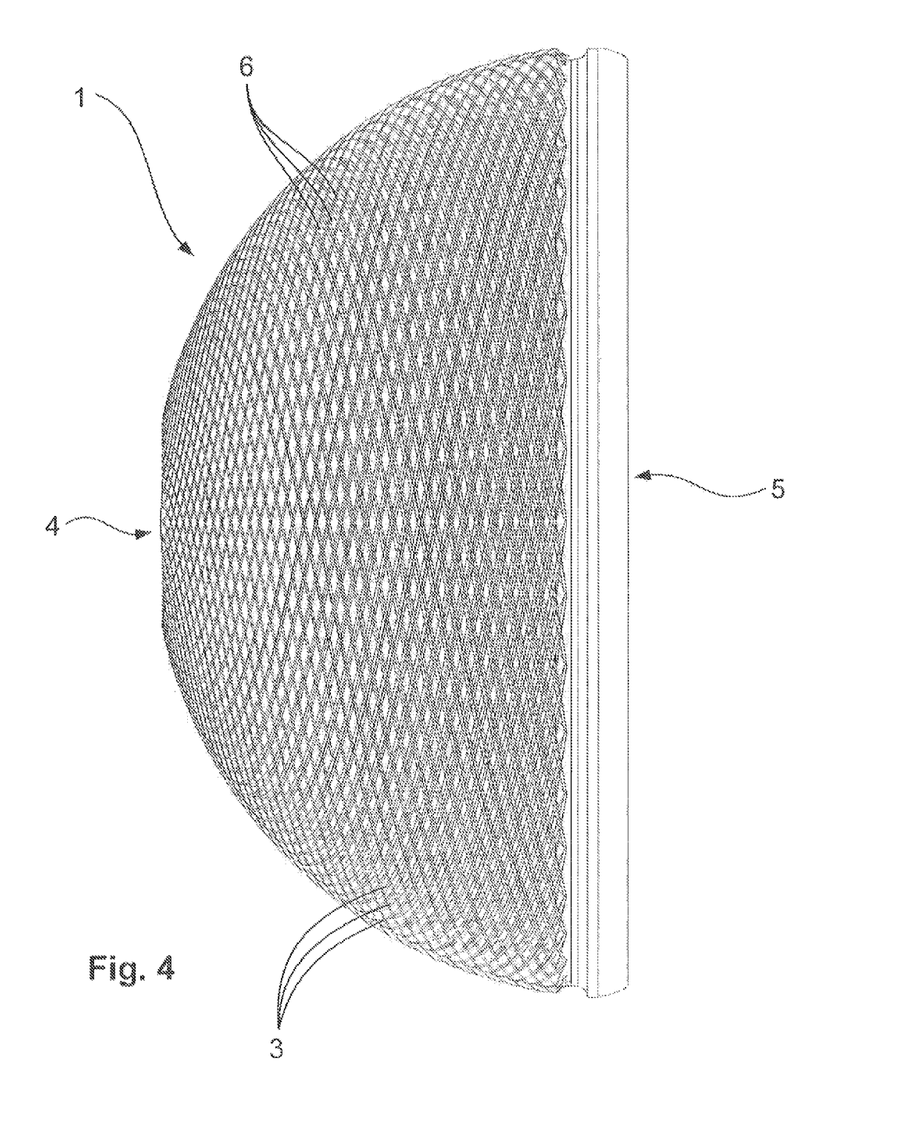
FIG. 4 shows a side view of the joint socket implant from FIG. 3.

FIGS. 3 and 4 show a plan and side view of a joint socket implant 1 with a region with a surface structure 2. The surface structure 2h as a multiplicity of structure elements 6, which are formed by the intersecting grooves 3. The grooves 3 have such curvature or such a profile that the pitch of the grooves 3 in relation to the circles of latitude, and hence an angle between a tangent of the groove curvature and a circle of latitude, increases continuously from the equator 5 to the pole 4. The grooves 3 are selected in such a way that the number of structure elements 6 on the equator 5 or a circle of latitude close to the equator is the same as on a circle of latitude close to the pole. The formed structure elements 6 have an approximately rhomboid area, which is delimited by the curved grooves 3.

Figure 5:
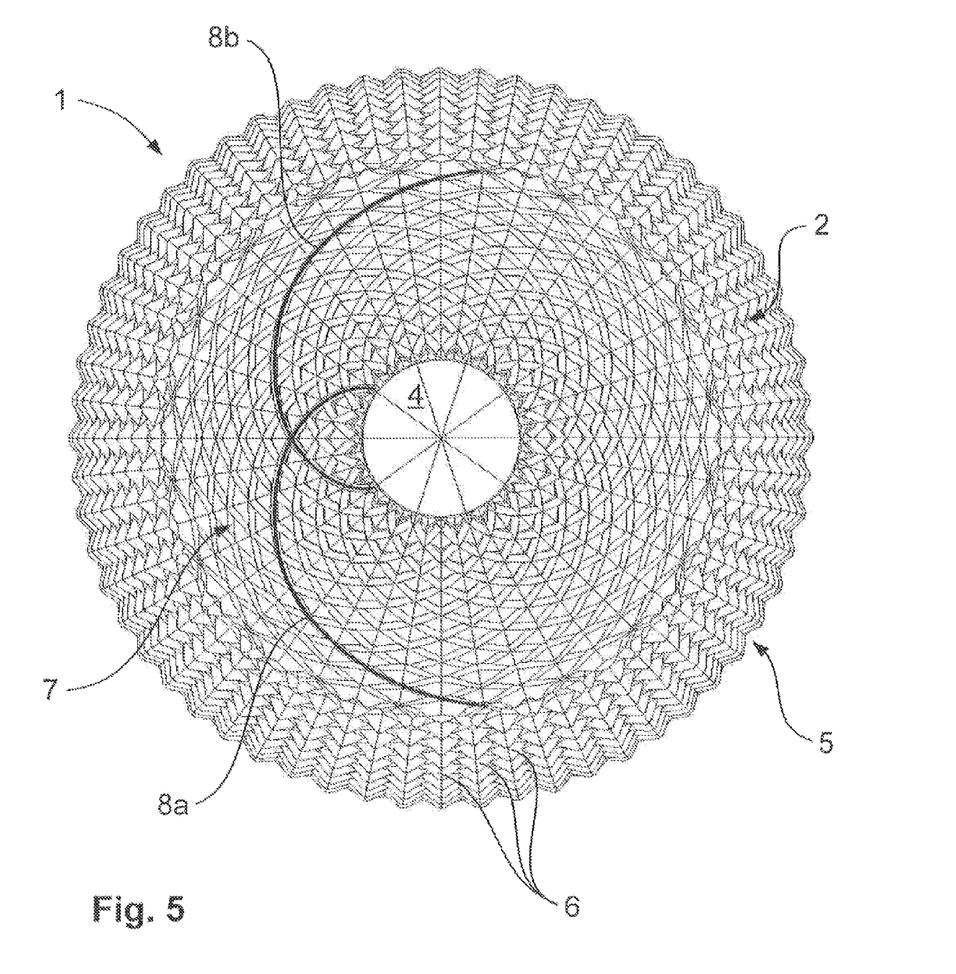
FIG. 5 shows a plan view of a joint socket implant with two regions with in each case different surface structures.
Figure 6:
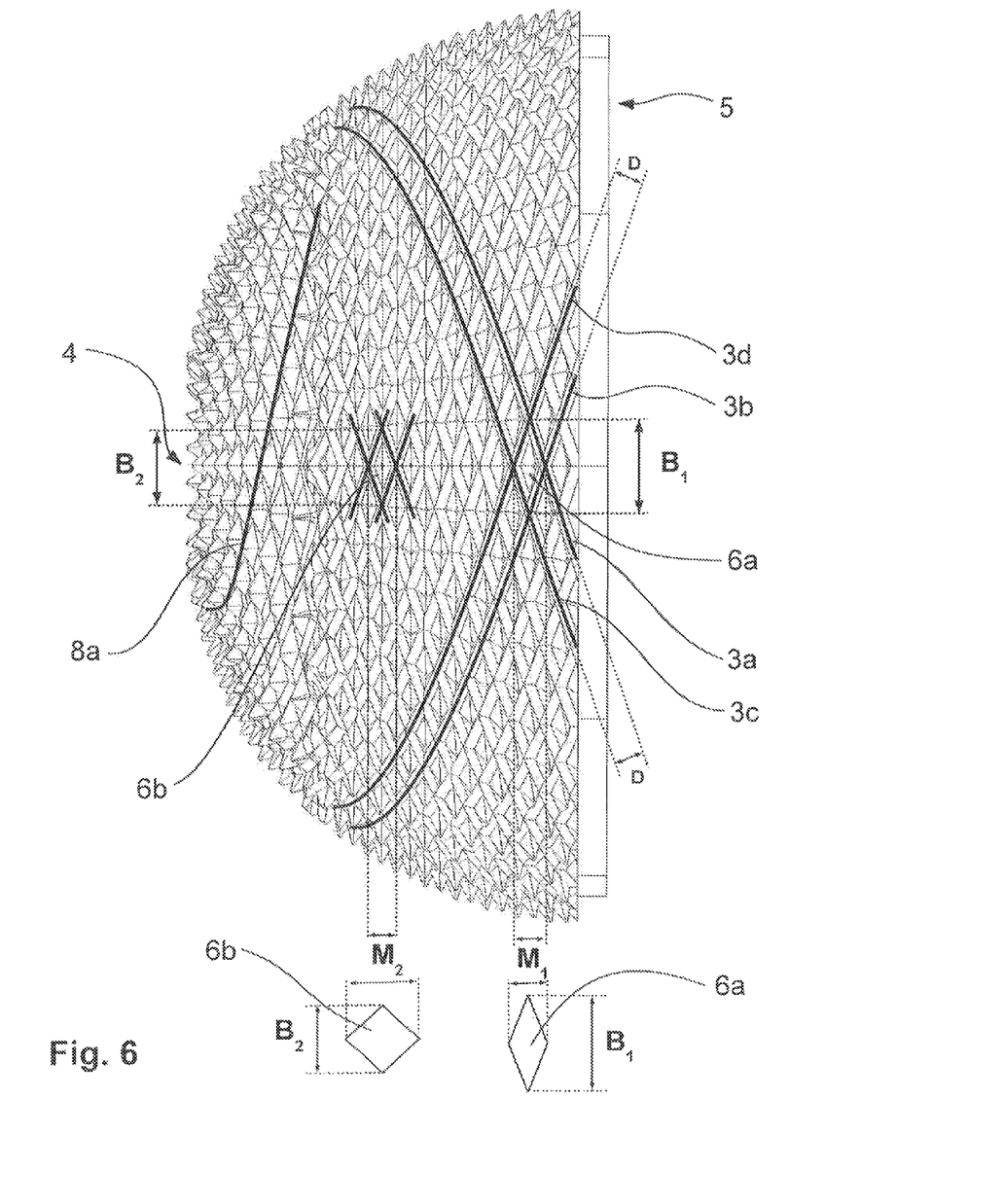
FIG. 6 shows a side view of the joint socket implant from FIG. 4.

FIGS. 5 and 6 show a plan and side view of a particularly preferred embodiment of the joint socket implant 1 according to the invention. This joint socket implant 1 comprises two regions with a surface structure 2, 7. The grooves 3a-3d of the first surface structure 2 differ from the grooves 8a, 8b of the second surface structure. By way of example, the number of grooves, the curvature extent, profile and/or depth thereof can differ. This also results in different shapes of the structure elements 6 in the two regions 2, 7. The curvature profile of the grooves 3a-3d, 8a, 8b is clearly visible from these figures. Furthermore, it can also be seen that the distance D between two grooves 3b and 3d with the same pitch direction, i.e. the perpendicular distance in respect of a tangent of one of the grooves, e.g. groove 3b, from the neighboring groove 3d, is constant over the whole length of the grooves.

It is also possible to see the change in the outlines of the structure elements 6 with increasing distance from the equator 5. Here, the length of the diagonals of the outlines parallel to the circles of latitude decreases from the equator in the direction of the pole, while the length of the diagonals parallel to the meridians increases.

This is depicted in FIG. 6 in an exemplary fashion using two structure elements 6a, 6b with approximately rhomboid outlines. Since the differences in the outlines of the two structure elements 6a, 6b is barely visible in the side view of FIG. 6 as a result of perspective distortion, the two structure elements 6a and 6b are shown qualitatively on the left-hand side of FIG. 6 for illustrative purposes. The outlines are depicted in a perpendicular plan view. The separate depiction of the outlines serves only for illustrating a tendency and, to this end, is depicted in a slightly exaggerated fashion.

The area of the structure element 6a close to the equator has a diagonal $B_1$ parallel to the circles of latitude which is longer than the diagonal $M_1$ parallel to the meridians. This length ratio of the diagonals changes with increasing distance from the equator 5. The structure element 6b close to the pole has a diagonal $B_2$ parallel to the circles of latitude which, in the illustration of FIG. 6, has approximately the same length as the diagonal $M_2$ parallel to the meridians. It is understood that the diagonal $B_2$ can also be shorter than the diagonal $M_2$.

Here, the length of the diagonal $B_2$ parallel to the circles of latitude of the structure element 6b close to the pole is shorter than the corresponding diagonal $B_1$ of the structure element 6a close to the equator, while the diagonal $M_2$ parallel to the meridians of the structure element 6b close to the pole is longer than the corresponding diagonal $M_1$ of the structure element 6a close to the equator.

Figure 7:
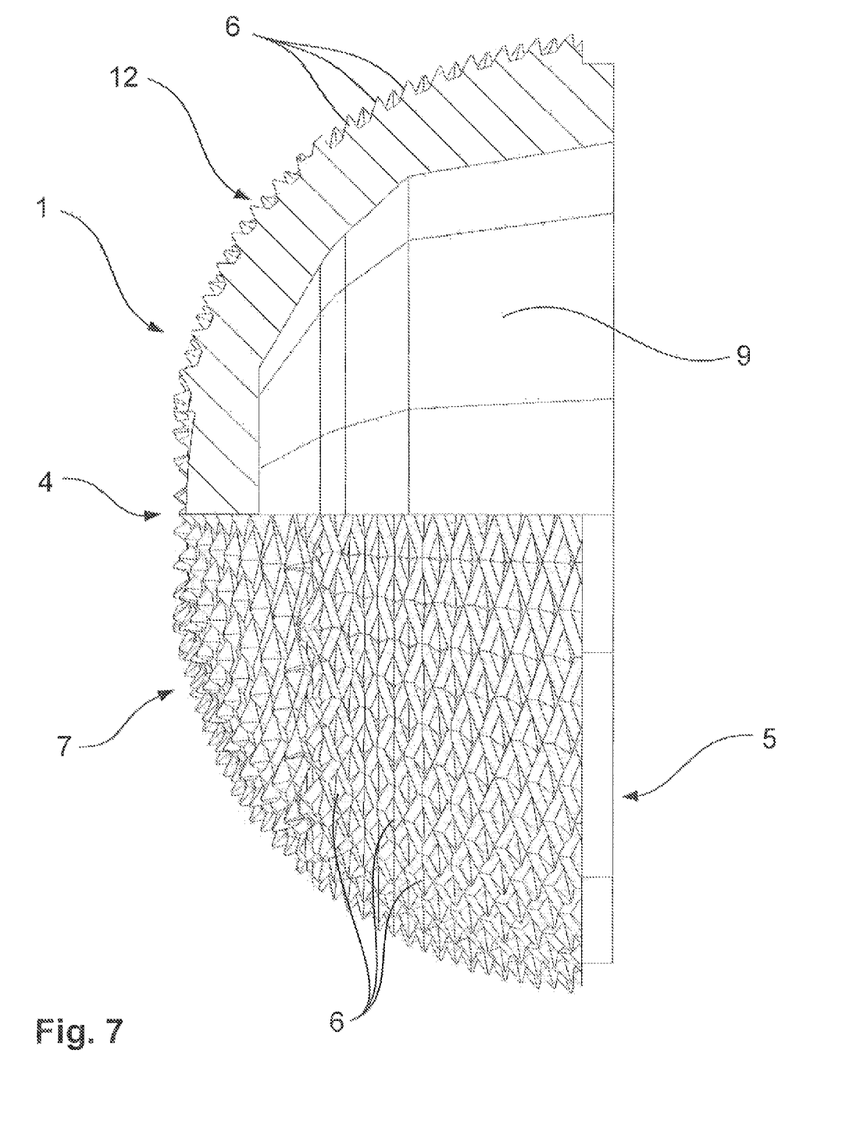
FIG. 7 shows a partial section through the joint socket implant from FIG. 4.

FIG. 7 shows a partial section through a joint socket implant 1. It can be seen from this figure that the joint socket implant 1 has an approximately concave inner face 9, which consists of several faces standing at an angle to one another. Furthermore, the joint socket implant 1 has a convex outer face 12. In this embodiment, only the convex outer face 12 has a surface structure with structure elements 6.

Figure 8:
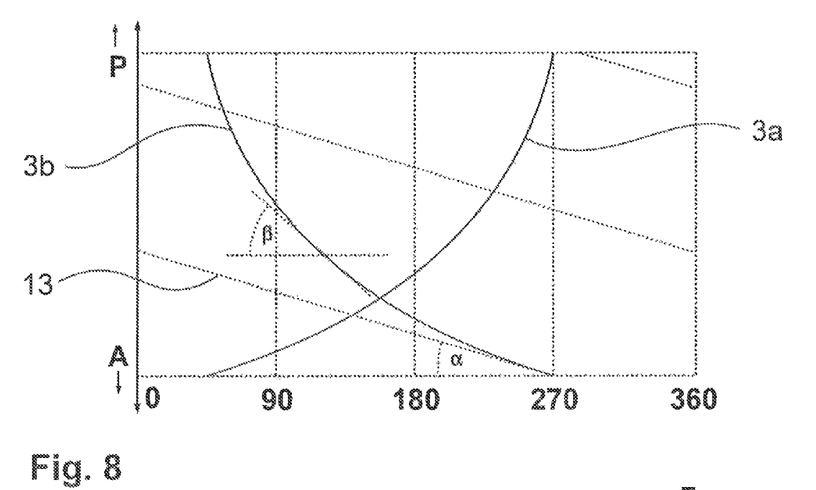
FIG. 8 shows a qualitative Mercator projection of two grooves with opposite pitch directions on the surface of a joint socket implant according to the invention.

FIG. 8 shows a qualitative Mercator projection of two grooves 3a, 3b on a surface 12 of a joint socket implant according to the invention with opposite pitches. Circumferential angles of the joint socket implant in relation to a pole axis are plotted on the horizontal x-axis. A latitudinal range between equator 5 and pole 4 is depicted on the y-axis perpendicular thereto. The dashed lines parallel to the y-axis represent selected meridians.

The depicted region is delimited and does not extend completely to the pole 4 or to the equator 5. A sphere loxodrome, i.e. lines on the sphere face which intersect all circles of latitude or meridians at the same angle, are known to extend as straight lines in such projections. A loxodrome 13 (dashed line), which has a constant pitch angle α, is shown in an exemplary fashion. Compared to this, it is possible to see the increasing pitch of the grooves 3 with increasing distance from the equator 5 in the direction P toward the pole 4.

A tangent of the groove 3a likewise includes the angle α toward the equator 5 with a circle of latitude in a region A. It emerges from the diagram in FIG. 8 that the pitch of the groove 3a increases and continuously breaks away in the direction P toward the pole 4 compared to the loxodrome 13, i.e. it has an increasing pitch. In an exemplary fashion, a further angle β is shown in respect of a circle of latitude closer to the pole, which further angle is included by a tangent of the intersection of the groove 3a with this circle of latitude and which further angle is greater than the angle α.

Figure 9:
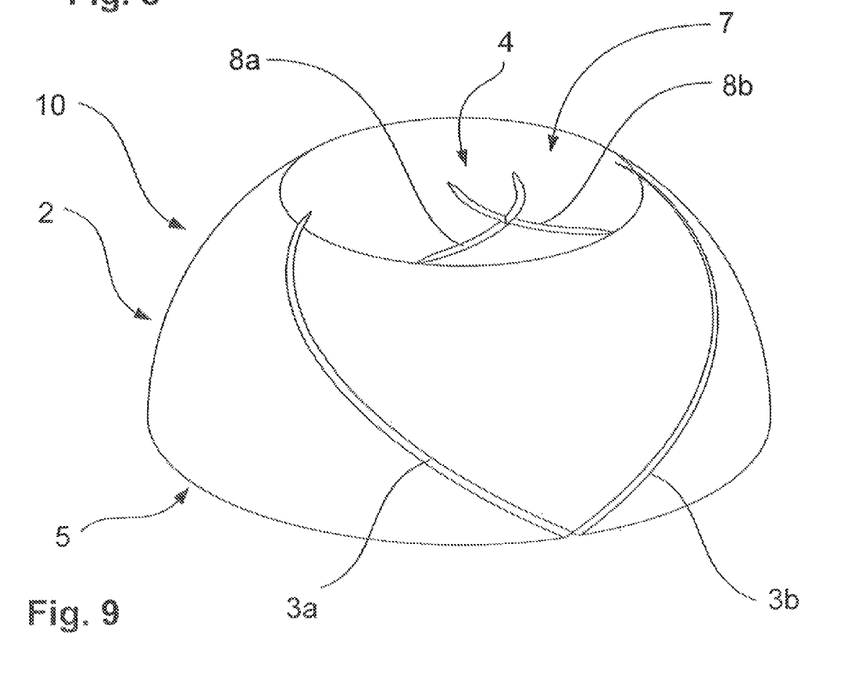
FIG. 9 shows an oblique view of an intermediate product during the production of a joint socket implant with individual grooves.

FIG. 9 shows an oblique view on an intermediate product 10 during the production of a joint socket implant 1 with two regions 2, 7 for a surface structure. Two grooves 3a and 3b (region 2) and grooves 8a and 8b (region 7) are respectively formed, e.g. milled, in the regions 2, 7. It can be seen from FIG. 9 that the grooves 3a, 3b extending from a region close to the equator toward the pole 4 end at the transition from the region 2 to the region 7, while the grooves 8a, 8b join at the transition and extend further in the direction toward the pole 4. It is also possible to see the increasing pitch of the grooves 3a, 3b and 8a, 8b with increasing closeness to the pole.

Figure 10:
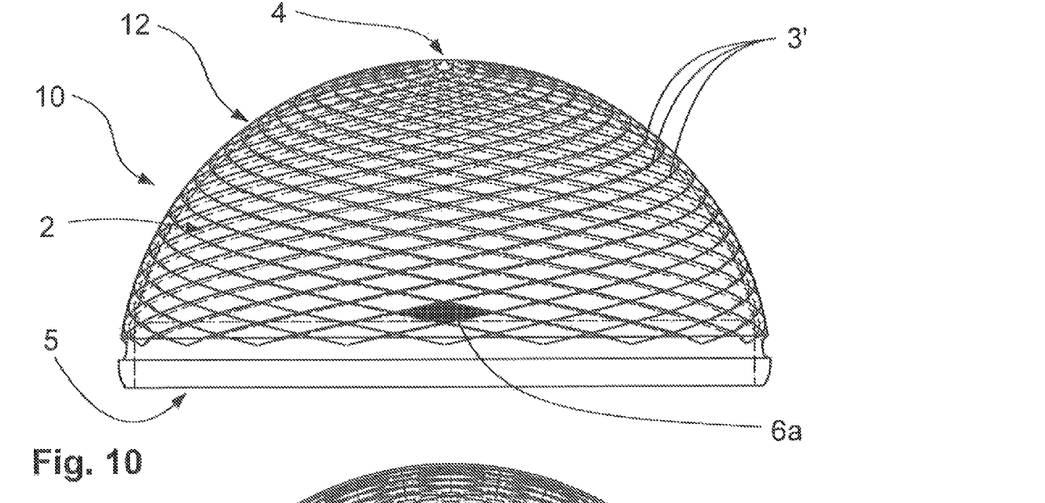
FIG. 10 shows a side view of a cap shell for a further embodiment of a joint socket implant according to the invention, with a plotted groove profile.
Figure 11:
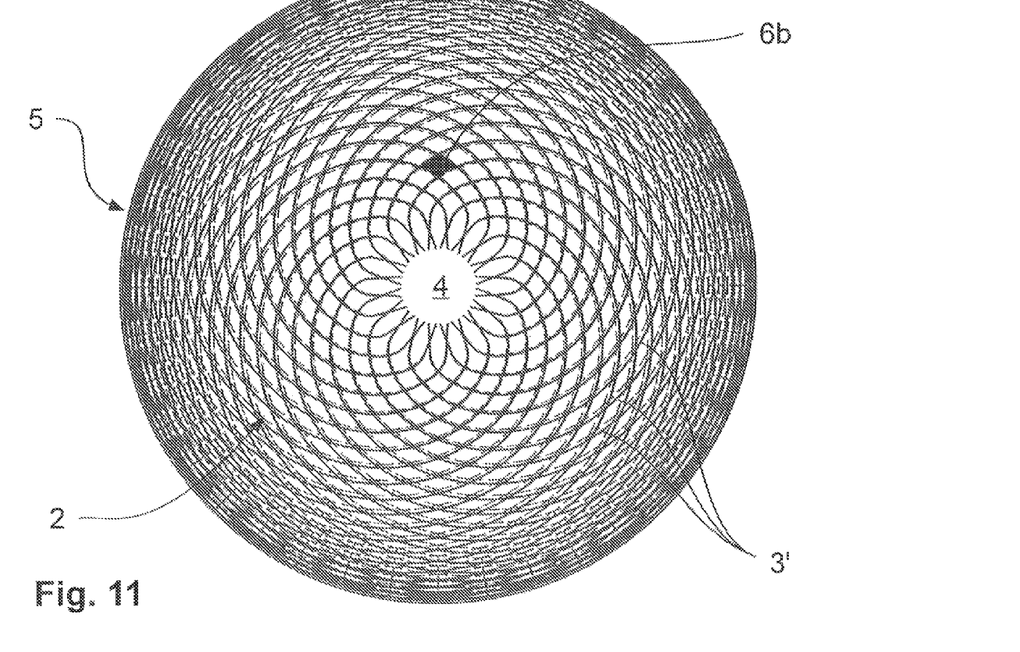
FIG. 11 shows a plan view on the cap shell as per FIG. 10.

FIGS. 10 and 11 show a side view and a plan view of an intermediate product 10 during the production of a joint socket implant 1. Cut lines 3' are depicted on an outer cap surface, along which cut lines the grooves 3 will subsequently be produced. A profile of the cut lines 3' close to the pole can be identified particularly well in FIG. 11, which are directed almost radially toward the pole 4 in the end regions close to the pole.

Likewise, for the further illustration of how the outline of structure elements, which are made later in the production by the grooves, changes with a distance from the pole, an outline of a structure element 6a close to the equator and also of a structure element 6b close to the pole has been plotted. In the side view of FIG. 10, the structure element 6a close to the equator is plotted in a largely frontal view. In the plan view of FIG. 11, the structure element 6b close to the pole can be identified in the largely frontal view. As a result, there is only an insignificant perspective distortion in both cases, as a result of which the outlines of the structure elements which change with the distance from the pole or from the equator can clearly be identified (see also FIG. 6 in this respect).

Figure 12:
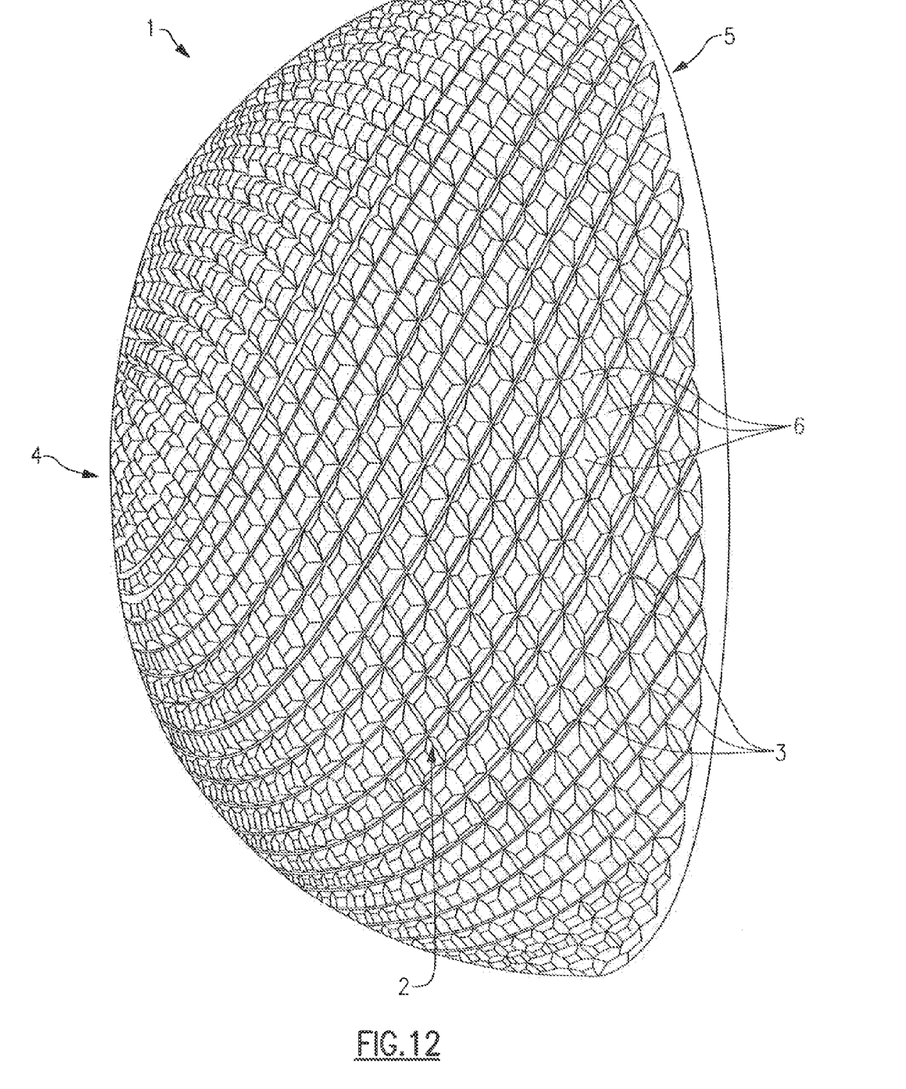
FIG. 12 shows a photographic side view of a joint socket implant according to the invention.

FIG. 12 shows a photographic side view of a joint socket implant 1, in which the constant width between neighboring grooves 3 can be identified. In this embodiment, the structure elements 6 are embodied as pyramid frustums.

The invention claimed is:

1. A joint socket implant in the form of a spherical cap shell having an equator and a pole, with a first region between the equator and the pole of the spherical cap shell having a surface structure which comprises a multiplicity of structure elements, which are formed by intersecting arrays of grooves with opposite pitches, wherein
    the number of structure elements on the equator or on a circle of latitude close to the equator is the same as on a circle of latitude close to the pole, and
    the grooves have such curvature that the pitch of the grooves in relation to the circles of latitude, and hence an angle between a tangent of the groove curvature and a circle of latitude, increases continuously from the equator to the pole.

2. The joint socket implant as claimed in claim 1, wherein two adjacent grooves in said region with the same pitch have a substantially constant distance from one another over their whole length.

3. The joint socket implant as claimed in claim 1, wherein the grooves have a constant depth in said region from the equator to the pole.

4. The joint socket implant as claimed in claim 1, wherein the angles between the grooves and any one circle of latitude are identical.

5. The joint socket implant as claimed in claim 1, wherein at least some of said grooves differ in shape, depth, width, or spacing.

6. The joint socket implant as claimed in claim 1, wherein the structure elements have the shape of a pyramid or a pyramid frustum, 7. The joint socket implant as claimed in claim 1, wherein the structure elements are inclined toward the equator.

8. The joint socket implant as claimed in claim 1, further comprising a second region with a surface structure formed by intersecting grooves.

9. The joint socket implant as claimed in claim 8, wherein the surface structures in the respective regions have different configurations.

10. The joint socket implant as claimed in claim 8, wherein the regions with surface structures have at least one of
    a different number of structure elements,
    structure elements which differ in size, shape or spacing.

11. The joint socket implant as claimed in claim 8, wherein the first region is close to the equator and the second region is close to the pole and has structure elements in the form of pyramids or pyramid frustums.

12. The joint socket implant as claimed in claim 1, wherein, in a region of the surface structure close to the equator, the grooves form an angle of less than 90° with a circle of latitude.

13. The joint socket implant as claimed in claim 12, wherein said angle is between from 10° to 60°.

14. The joint socket implant as claimed in claim 1, wherein the at least one region with a surface structure on the equator or on a circle of latitude close to the equator and on a circle of latitude close to the pole, respectively, has 10 to 100 structure elements.

15. The joint socket implant as claimed in claim 1, wherein the structure elements have outlines with side lengths of 0.2-5 mm.

16. The joint socket implant as claimed in claim 1, wherein each of the structure elements has an outline whose shape is a rhombus having latitudinal and longitudinal diagonals, wherein the length of the latitudinal diagonals decreases from the equator in the direction of the pole, while the length of the longitudinal diagonals increases.

17. The joint socket implant as claimed in claim 1, wherein the grooves have a symmetric cross section.

18. The joint socket implant as claimed in claim 1, wherein the grooves have an asymmetric cross section.

* * * * *